(12) United States Patent
Jakubowicz et al.

(10) Patent No.: US 7,312,084 B2
(45) Date of Patent: Dec. 25, 2007

(54) TANDEM INCUBATOR FOR CLINICAL ANALYZER

(75) Inventors: Raymond Francis Jakubowicz, Rush, NY (US); Gary Steven Hartman, Spencerport, NY (US); Johannes Jacobus Porte, Webster, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 273 days.

(21) Appl. No.: 09/904,692

(22) Filed: Jul. 13, 2001

(65) Prior Publication Data

US 2003/0017613 A1    Jan. 23, 2003

(51) Int. Cl.
GO1N 35/00    (2006.01)

(52) U.S. Cl. ............... 436/43; 436/54; 436/47; 436/48; 436/49; 422/62; 422/63; 422/64; 422/67

(58) Field of Classification Search ............... 436/43, 436/45, 47–49, 164; 422/62–64, 67
See application file for complete search history.

(56) References Cited

U.S. PATENT DOCUMENTS

| | | | |
|---|---|---|---|
| 3,193,358 A | 7/1965 | Baruch | |
| 3,252,330 A | 5/1966 | Kling | |
| 3,589,867 A | 6/1971 | Heinz et al. | |
| 3,636,777 A | 1/1972 | Frank et al. | |
| 4,067,694 A | 1/1978 | Blakely et al. | |
| 4,123,173 A | 10/1978 | Bullock et al. | |
| 4,152,390 A | 5/1979 | Nosco et al. | |
| 4,170,625 A | 10/1979 | Welch | |
| 4,184,936 A | 1/1980 | Paul et al. | |
| 4,214,968 A | 7/1980 | Battaglia et al. | |
| 4,219,529 A | 8/1980 | Tersteeg et al. | |
| 4,234,538 A | 11/1980 | Ginsberg et al. | |
| 4,234,539 A | 11/1980 | Ginsberg et al. | |
| 4,234,540 A | 11/1980 | Ginsberg et al. | |
| 4,257,862 A | 3/1981 | Schnipelsky et al. | |
| 4,271,123 A | 6/1981 | Curry et al. | |
| 4,296,069 A | 10/1981 | Smith et al. | |
| 4,296,070 A | 10/1981 | Montalto et al. | |
| RE31,108 E | 12/1982 | Ginsberg et al. | |
| RE31,149 E | 2/1983 | Ginsberg et al. | |
| RE31,150 E | 2/1983 | Ginsberg et al. | |
| 4,517,160 A | 5/1985 | Galle et al. | |
| 4,552,458 A | 11/1985 | Lowne | |
| 4,558,946 A | 12/1985 | Galle et al. | |
| 4,568,519 A * | 2/1986 | Hamilton et al. | 422/64 |
| 4,584,275 A | 4/1986 | Okano et al. | |

(Continued)

FOREIGN PATENT DOCUMENTS

EP    0 290 218    7/1996

*Primary Examiner*—Lyle A Alexander
(74) *Attorney, Agent, or Firm*—Marjama Muldoon Blasiak & Sullivan LLP

(57) ABSTRACT

An incubator includes an incubator ring assembly having at least two concentric rings supported for rotation about a common axle defining an axis of rotation. Each concentric ring includes a plurality of circumferentially defined load positions, each load position being sized for accommodating a test sample. At least one test station is arranged in relation to the plurality of load positions to selectively test a test sample, the test samples being are sequentially shuttled into and out of load positions of at least one of the concentric rings to increase the overall throughput of the analyzer.

27 Claims, 12 Drawing Sheets

U.S. PATENT DOCUMENTS

| | | |
|---|---|---|
| 4,634,575 A | 1/1987 | Kawakami et al. |
| 4,678,752 A | 7/1987 | Thorne et al. |
| 4,781,891 A | 11/1988 | Galle et al. |
| 4,814,144 A | 3/1989 | Edelmann et al. |
| 4,844,887 A | 7/1989 | Galle et al. |
| 4,963,333 A | 10/1990 | Shaw et al. |
| 4,965,049 A | 10/1990 | Lillig et al. |
| 5,034,191 A | 7/1991 | Porte |
| 5,051,238 A | 9/1991 | Umetsu et al. |
| 5,073,342 A | 12/1991 | Porte et al. |
| 5,081,038 A | 1/1992 | Sugaya et al. |
| 5,160,702 A | 11/1992 | Kopf-Sill et al. |
| 5,244,633 A * | 9/1993 | Jakubowicz et al. .......... 422/64 |
| 5,270,210 A | 12/1993 | Weyrauch et al. |
| 5,419,871 A | 5/1995 | Muszak et al. |
| 5,447,690 A | 9/1995 | Sugaya |
| 5,482,861 A | 1/1996 | Clark et al. |
| 5,501,984 A | 3/1996 | Hofstetter et al. |
| 5,507,388 A | 4/1996 | Kildal et al. |
| 5,523,056 A | 6/1996 | Miller |
| 5,639,425 A | 6/1997 | Komiyama et al. |
| 5,672,512 A | 9/1997 | Shaw |
| 5,827,478 A | 10/1998 | Carey et al. |
| 5,882,594 A | 3/1999 | Kawaguchi et al. |
| 6,136,270 A | 10/2000 | Maes et al. |
| 6,156,565 A | 12/2000 | Maes et al. |
| 6,190,617 B1 | 2/2001 | Clark et al. |

* cited by examiner

TANDEM INCUBATOR FOR CLINICAL ANALYZER

FIELD OF THE INVENTION

The invention relates to the field of analytical sample testing and in particular to a sequential tandem incubator for a clinical analyzer.

BACKGROUND OF THE INVENTION

Clinical analyzers typically include at least one incubator that is used for the processing of patient samples. A typical "dry" chemistry incubator, for example, is defined by a rotor assembly that includes a single rotatably driven ring having a plurality of circumferentially disposed load stations. Each of the load stations are sized to accommodate a dry element onto which a quantity of patient sample can be metered.

According to at least one version of a dry-type incubator, the slide elements are supplied one at a time to a metering station which is adjacent to the incubator. After sample fluid has been metered, the slide element is shuttled or otherwise introduced into an empty load station of the incubator, such as through use of a reciprocating pusher blade as the rotor assembly advances the next empty load station into position for receiving the next metered slide element.

Various types of sample testing, including potentiometric, rate chemistry, and endpoint tests, may be required for any given patient sample, necessitating both different incubation intervals and test apparatus within the incubator. Therefore, scheduling for multiple types of patient sample tests will certainly and significantly affect the overall throughput of the device. Though several dedicated incubator assemblies could be provided within an analyzer as a potential solution to the throughput problem, there is an equally competing need in the field to keep the overall footprint of the clinical analyzer as small as possible.

Attempts have been made in order to improve the efficiency of incubator assemblies in general. For example, referring to FIG. 1 and as described by U.S. U.S. Pat. No. 5,523,056 to Miller, an incubator assembly 50 includes a pair of vertically stacked rotor assemblies 54, 58, each of the rotor assemblies being accessible to a metering station (not shown) by means of an elevator that permits an additional number of dry slide elements to be accommodated. This vertical arranged stacking, according to the teachings of this reference, saves available space for the analyzer. Other attempts to improve efficiency have incorporated multiple read stations within the incubator assembly to handle the different types of tests that are required.

SUMMARY OF THE INVENTION

It is a primary object of the present invention to overcome the above noted problems of the prior art.

It is another primary object of the present invention to increase the overall throughput of an incubator assembly without significantly increasing the size thereof.

It is yet another primary object of the present invention to provide an incubator assembly which does not require a multiple number of test read stations.

Therefore and according to a preferred aspect of the present invention, there is disclosed an incubator including an incubator housing having at least one load station for accommodating at least one test sample and at least one stationary read station which is disposed within the incubator housing. First drive means are provided for driving at least one of said at least one test sample and the load station in a first direction. The at least one load station includes at least two movable load positions which are arranged in a second direction, the second direction being substantially orthogonal to said first direction. Second drive means selectively drive at least one of said load positions and said at least one test sample accommodated therein in the second direction with respect to the at least one read station for reading said at least one test sample.

According to a preferred embodiment, the incubator includes a ring assembly including at least two concentric rings disposed within a housing. Each of the concentric rings are preferably supported for rotation about a common center axis of rotation, and include a plurality of circumferentially disposed load stations. First drive means drives each of the load stations circumferentially about the axis of rotation in order to incubate test elements or sample containers, while a second drive means selectively and radially drives at least one of the test elements or sample containers or at least one corresponding load station in order to move one of the test elements or sample containers for analyte-correlated signal detection at a read station. More particularly, the second drive means moves or transfers at least one test element or sample container between a first load position and a second load position of a load station.

In a preferred embodiment, a read station is disposed with regard to one of the concentric rings such that a first test element or sample container can be read when the ring is rotated into alignment with the first test element. Following this read step, a second radially adjacent test element or sample container can be transferred by the second drive means into alignment with the read station for reading thereof.

According to a preferred embodiment, sample fluid is metered onto test elements and at least one reciprocating pusher blade serves as the second drive means to radially transfer at least one test element from one load position to an adjacent load position on the ring assembly for alignment with the read station. Each of the test elements can then be disposed of; that is, the test elements can be dumped from the incubator and new test elements can be added. In a preferred embodiment, a pair of test elements can be added to the incubator housing simultaneously using a single or multiple pusher blades. An additional number of pusher blades disposed about the periphery of the ring assembly can be used to shift the radial position of the test elements following initial placement within the incubator housing, as needed, in order to increase the efficiency and throughput of the overall assembly.

The incubator can also include third drive means for selectively and radially removing at least one test element or sample container from a load station of the ring assembly for later reinsertion therein.

According to a preferred embodiment, single read stations are provided for colorimetric and potentiometric sample testing, respectively, in which the slide elements can be transferred between concentric rings of the ring assembly. Furthermore, each of the concentric rings can be independently driven to further maximize efficiency and test scheduling.

According to a preferred aspect of the invention, there is disclosed an incubator for use in a clinical analyzer, said incubator comprising:

an incubator ring assembly supported for rotation about an axis of rotation, said ring assembly including a plurality of circumferentially defined load stations, each said load station having at least two adjacent radial load positions for receiving test elements or sample containers;

at least one read station for reading at least one test element or sample container at a read position:

first drive means operatively connected to said incubator ring assembly for rotating said ring assembly about said axis of rotation, said at least one said read station being disposed such that a first plurality of circumferentially disposed load positions can be selectively aligned with said read position; and second drive means for radially moving a test element or sample container from at least one load position of a load station into the read position.

According to yet another preferred aspect of the present invention, there is disclosed a clinical analyzer comprising an analyzer housing and an incubator disposed within the analyzer housing. The incubator includes at least one load station for accommodating at least one test element or sample container and at least one read station. First drive means are provided for driving at least one of said at least one test element or sample container and said load station in a first direction, said at least one load station having at least two load positions arranged in a second direction, said second direction being substantially orthogonal to said first direction; and second drive means for selectively driving at least one of said load positions and said at least one test element or other sample container accommodated therein with respect to said read station for testing said at least one test element or sample container.

According to yet another preferred aspect of the present invention, there is provided a method of incubating and reading test samples for a clinical analyzer, said incubator comprising at least one load station for accommodating at least one test element or sample container and a read station disposed within an incubator housing, the method comprising the steps of:

driving at least one of test element or sample container and said load station in a first direction, said at least one load station having at least two load positions arranged in a second direction, said second direction being substantially orthogonal to said first direction; and selectively driving at least one said load station and said at least one test element or sample container accommodated therein in the second direction to locate at least one test element or sample container relative to said read station for reading said at least one test element or sample container.

An advantage of the present invention is that providing an incubator having concentric multiple ring components with adjacent radial load positions and a plurality of shuttle assemblies to permit the interchange of test samples between these positions increases the number of potential opportunities to schedule and efficiently perform multiple types of tests. As a result, the overall efficiency of the incubator is maximized and the overall throughput of an analyzer utilizing the incubator is increased.

It will be readily apparent from the discussion that follows that the incubator can include element receiving stations which can be driven using rotary or linear movement (a first direction) and radial or linear movement (a second direction) so as to maximize throughput with a minimum number of read stations.

Another advantage of the present invention is that the coordination of elements or sample containers which are incubated and tested is far more flexible and efficient than any previously known apparatus.

Yet another advantage is that the herein described incubator includes single read stations for performing potentiometric and calorimetric sample testing, respectively, thereby simplifying overall assembly and cost.

These and other objects, features, and advantages will become readily apparent from the following Detailed Description which should be read in conjunction with the accompanying drawings.

DETAILED DESCRIPTION

The following description relates to specified embodiments of a sequentially loaded incubator made in conjunction with the present invention. Throughout the course of discussion, certain terms such as "inner", "outer", "lateral", "vertical", "horizontal", "upper", "lower" and the like are used to provide a frame of reference with regard to the accompanying drawings. These terms, however, except as indicated otherwise, should not be construed as limiting with regard to the herein claimed invention.

Also throughout the discussion, the term "element" is used in conjunction with a test sample. As defined herein, this term refers to dry slide elements as well as any other form of sample container. It will become readily apparent that this patent recites advantageous positioning of such containers in an incubator (rotary, linear or other) in order to improve throughput.

For purposes of background and to facilitate the following discussion, the following relates primarily to a "dry" incubator for use in a mainframe, desktop, or other type of clinical analyzer apparatus. The incubator according to each of the embodiments uses dry slide elements onto which a patient sample is metered. These slide elements are such as described in U.S. Pat. No. 3,992,158 to Przybylowicz et al., the entire contents of which is hereby incorporated by reference. For purposes of the following discussion, there are generally two different types of slide elements, each relating to a form of patient sample testing that is required. A "potentiometric" slide element 140, FIG. 6, such as described by U.S. Pat. Nos. 4,184,936 (Paul, et al.) and 4,214,968 (Battaglia, et al.), incorporated herein in their entirety, includes a pair of electrodes which can be interfaced with an electrometer or other suitable test apparatus capable of detecting an electrical property produced by a deposited test sample. A "colorimetric" slide element 144, FIG. 8, on the other hand, is capable of being read by a reflectometer or other suitable apparatus capable of detecting an optical property produced by or deposited onto the element through a read area provided on the slide element 144 which is aligned with an optical window of the testing device. Colorimetric slide elements are further categorized as to the type of testing required. Endpoint testing, for example, requires only a single optical read after a predetermined incubation interval, while rate chemistry tests require multiple optical reads during various points of an incubation cycle.

Figure 1:
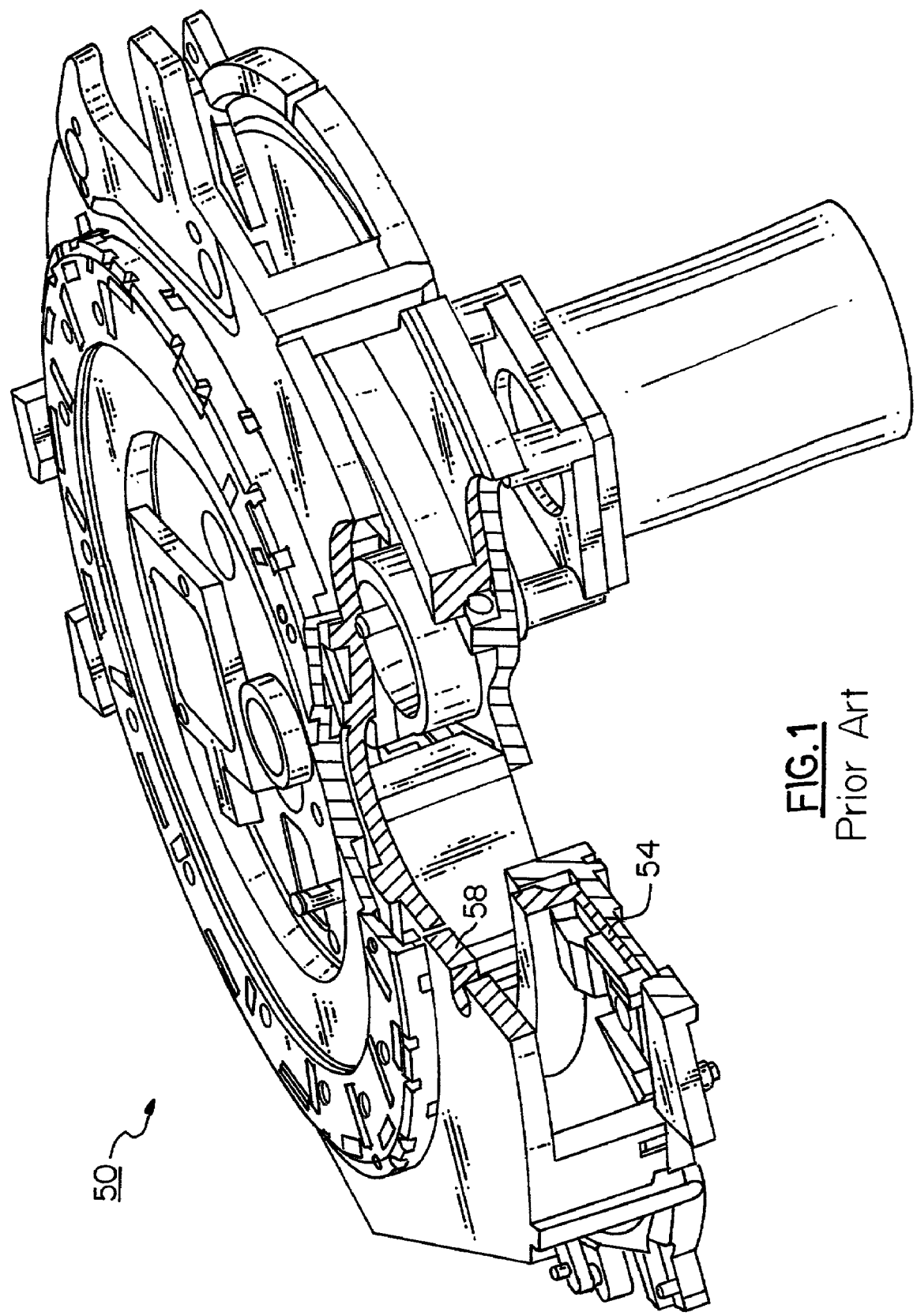
FIG. 1 is a partial top perspective view of an prior art incubator.
Figure 2:
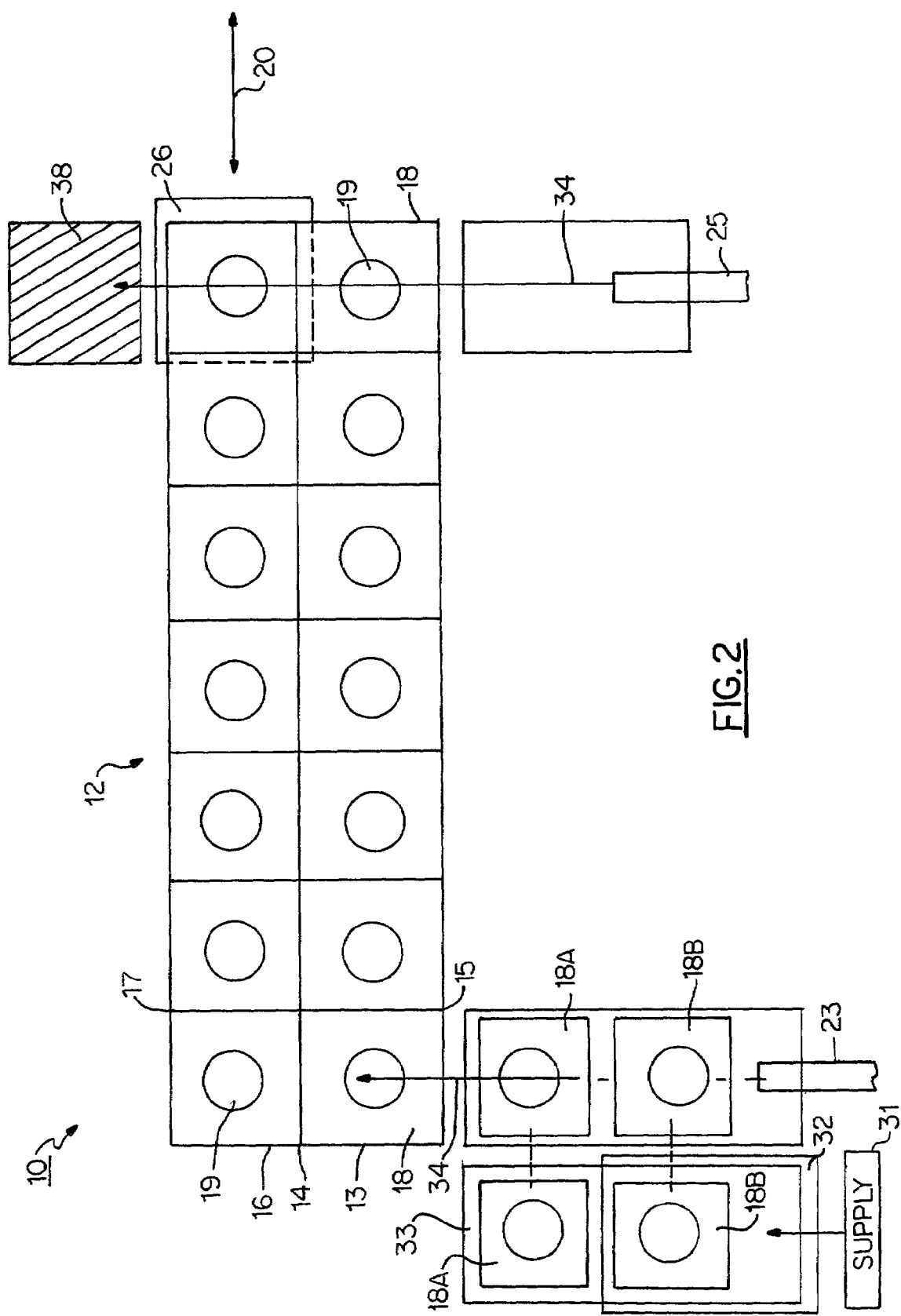
FIG. 2 is a simplified partial top view of the interior of an incubator made in accordance with a first embodiment of the present invention.

Referring to FIG. 2, a first embodiment of an incubator assembly 10 illustrating a number of the essential concepts of the present invention is depicted in simplified form. Only the interior of the incubator assembly 10 is shown and described herein for reasons of clarity.

A linear array 12 of load stations 14 are arranged along a first direction 20. Each load station 14 includes a pair of slots or receiving areas 15, 17 that are arranged along a second direction 34. As is evident in FIG. 2, the second direction 34 is substantially perpendicular to the first direction 20. At least one row 13, 16 of receiving areas 15, 17 of the linear array 12 are capable of rectilinear movement along the first direction 20 through use of a drive belt (not shown) or other suitable conventional means. That is to say, each of the rows 13, 16 are capable of either independent or coupled movement along the first direction 20. A read station 26, is stationarily disposed at one end of the incubator 10, the read station including a testing device (not shown), such as a reflectometer or other suitable testing apparatus, which examines an optical or other property of a test element. The read station 26 is disposed beneath the movement plane of the linear array 12 of load stations 14.

Each load station 14 is sized to receive a pair of dry slide elements 18 such as those described in U.S. Pat. No. 3,992,158 to Przybylowicz et al., the entire contents of which is hereby incorporated by reference. Each of the receiving areas 15, 17 of load station 14 includes respective openings 19 which correspond to a read area of a slide element 18 onto which a patient sample is first metered or dispensed at a metering station 32. As a slide element 16, 18 is moved into the read position 26, the opening 19 is aligned with the testing device. Adjacent the read station 26 and oppositely disposed along the second direction 34 are an eject slot or dump station 38 and a slide transferring device 25, respectively. Another slide element transferring device 23 is located at the opposite end of the incubator 10 which is disposed in parallel with the slide transferring device 25 to permit movement of slide elements 18 along the second direction 34 as described herein.

In operation and according to this embodiment, a pair of slide elements 18A, 18B can be simultaneously loaded into the incubator 10 and into respective empty receiving positions 15, 17 of a load station 14 using the slide transferring device 23. Each of the slide transferring devices 23, 25 shown include a reciprocating pusher blade, shown partially in FIG. 2, or other suitable means.

A first slide element 18A is shuttled to the metering station 32 from a slide supply 31 and sample fluid is metered from a metering head (not shown). The specifics of metering a sample fluid onto a dry slide element is conventionally known and does not form an essential part of the invention. Therefore, no further discussion is required. Following metering, the slide element 18A is advanced in the second direction 34 using a slide element transferring device (not shown), such as a reciprocating pusher blade, which engages the side edge of the element to advance the slide element to a staging position 33. In the staging position, the spotted slide element 18A is permitted to dry while a second slide element 18 is advanced from the slide supply 31 and is metered at the metering station 32. As noted, the details relating to metering of a patient sample fluid and a metering mechanism are conventionally known and do not form a significant part of the present invention.

Following the metering of sample fluid onto each of the slide elements 18A. 18B, each of the slide elements are shuttled using a linear shuttle, a linear pusher, belt or other conventionally known means into a load position adjacent the slide transferring device 23. Each of the slide elements 18B, 18A are then simultaneously loaded into respective receiving areas 15, 17 of the linear array 12.

Each of the rows of the linear array 12 are then advanced in the first direction 20 to advance additional empty receiving areas 15, 17 for loading of additional slide elements 18A, 18B in the same manner.

It should be noted that the only slide elements illustrated according to this embodiment are colorimetric slide elements for ease of illustration. As noted, these slide elements may require rate chemistry or endpoint tests. In brief, endpoint tests simply require a single optical read at the conclusion of an incubation interval while rate chemistry tests require multiple read operations during a separate incubation interval. Therefore, for purposes of the herein described invention, the slide elements designated as 18A may require either rate chemistry or endpoint chemistry tests and are loaded into row 16 of the linear array 12, while the slide elements designated 18B require end point and are positioned into the row 13.

The linear array 12 is reciprocated along the first direction 20, thereby permitting the slide element 18A to be read at the read station 26 an appropriate number of times. Following the final required read, the slide transferring device 25, such as a slide pusher blade, advances the slide element 18B into the read station 26, and shuttles the slide element 18A into the eject slot 38 for disposal. Depending on the tests required on the slide element 18B, the slide transferring device can again be used to displace the slide element 18B following the read to the eject slot 38 or the slide element 18B may remain for further testing and incubation. As a result, either one or two empty slots will be created.

It will be readily apparent that variations of this apparatus are possible. For example an additional read station could be provided including an electrometer for testing potentiometric slide elements. According to another alternate design, slide transferring device 23 could be positioned adjacent to slide transferring device 25, in order to fill empty load positions more efficiently.

It should be further noted that the above assembly, and others described herein, also may not be limited to utilization of dry slide elements; for example, liquid test samples could be retained within test receptacles (not shown) and moved relative to a read station which for example includes a spectrophotometer (not shown) or other apparatus. Therefore, and despite the fact "elements" are recited in the following discussion and are claimed as such it should be noted that as noted the term elements implies slide elements as well as other sample containers.

Referring to FIGS. 3-12, an incubator 100 in accordance with a preferred second embodiment of the invention includes a ring assembly 104 having a pair of concentric rings; namely, a first or inner ring 108 and a second or outer ring 112. Each of the inner and outer rings 108, 112 include a plurality of circumferentially spaced incubation positions.

According to this embodiment, the inner ring 108 is defined by a circular platen consisting of an array of pairs of radially adjacent slide element positions 116, 118, while the outer ring 112 includes a single circular array of slide element positions 122. A plurality of circumferential load stations are therefore defined, each load station being made up of an inner slide element position 116 and a middle or intermediate slide element position 118 each provided on the inner ring 108, as well as an outer slide element position 122 provided on the outer ring 112. A total of thirty-six (36) slide element positions are provided for each ring 108, 112, though it should be readily apparent that this parameter can easily be varied depending on the application.

Figure 7:
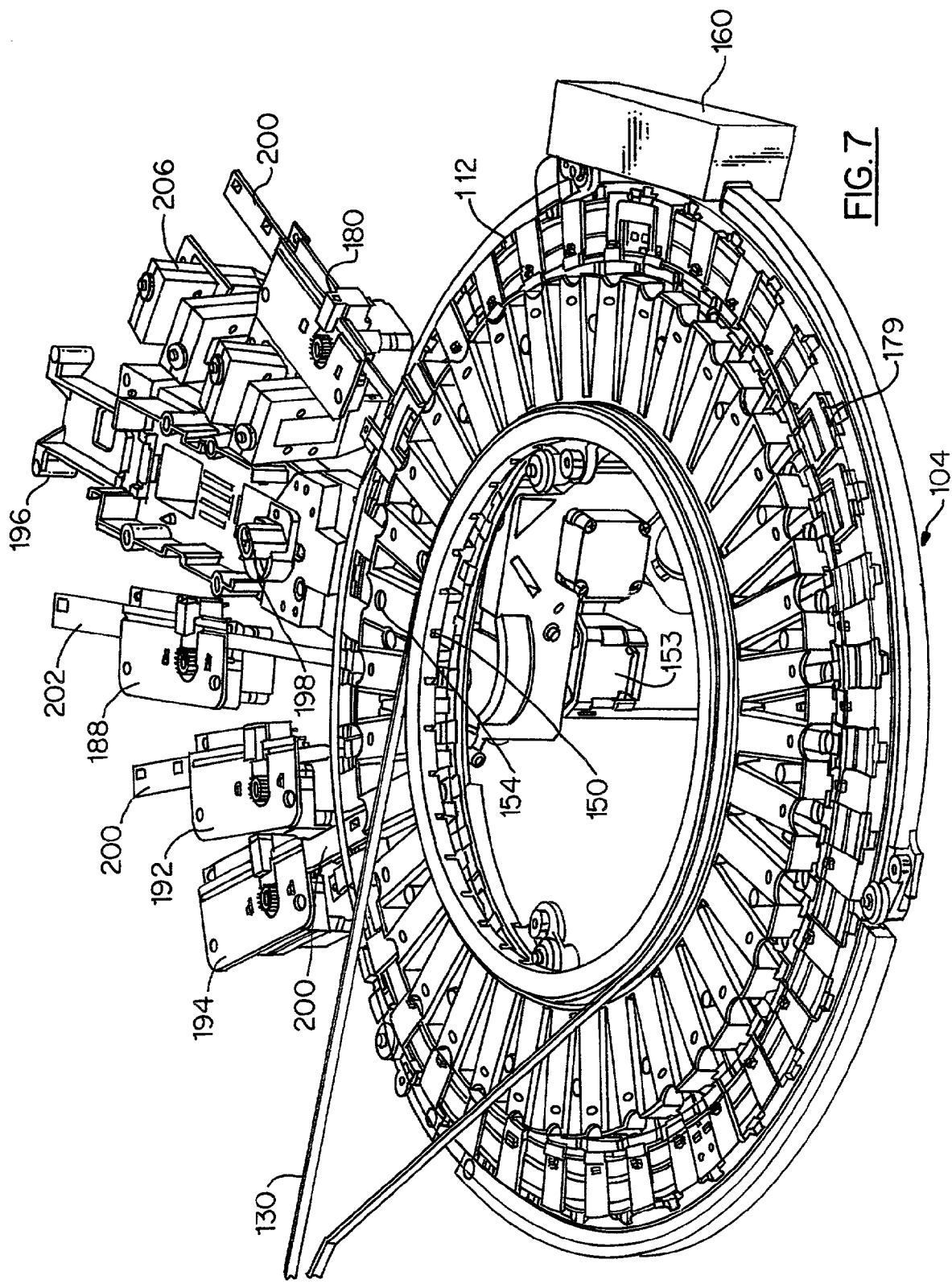
FIG. 7 is a partial top perspective view of the incubator of FIGS. 3-6, including the metering station.

Each of the inner and intermediate slide element positions 116, 118 defined by the inner ring 108 include a through opening 111 that permits read access by a reflectometer or other device capable of detecting an optical property of a test sample. The reflectometer 153, FIG. 7, is located beneath the inner ring 108 at an inner read station 150 as described below. According to this specific embodiment, no openings are provided for any of the outer slide element positions 122 of the outer ring 122, for reasons which will become apparent below.

Figure 3:
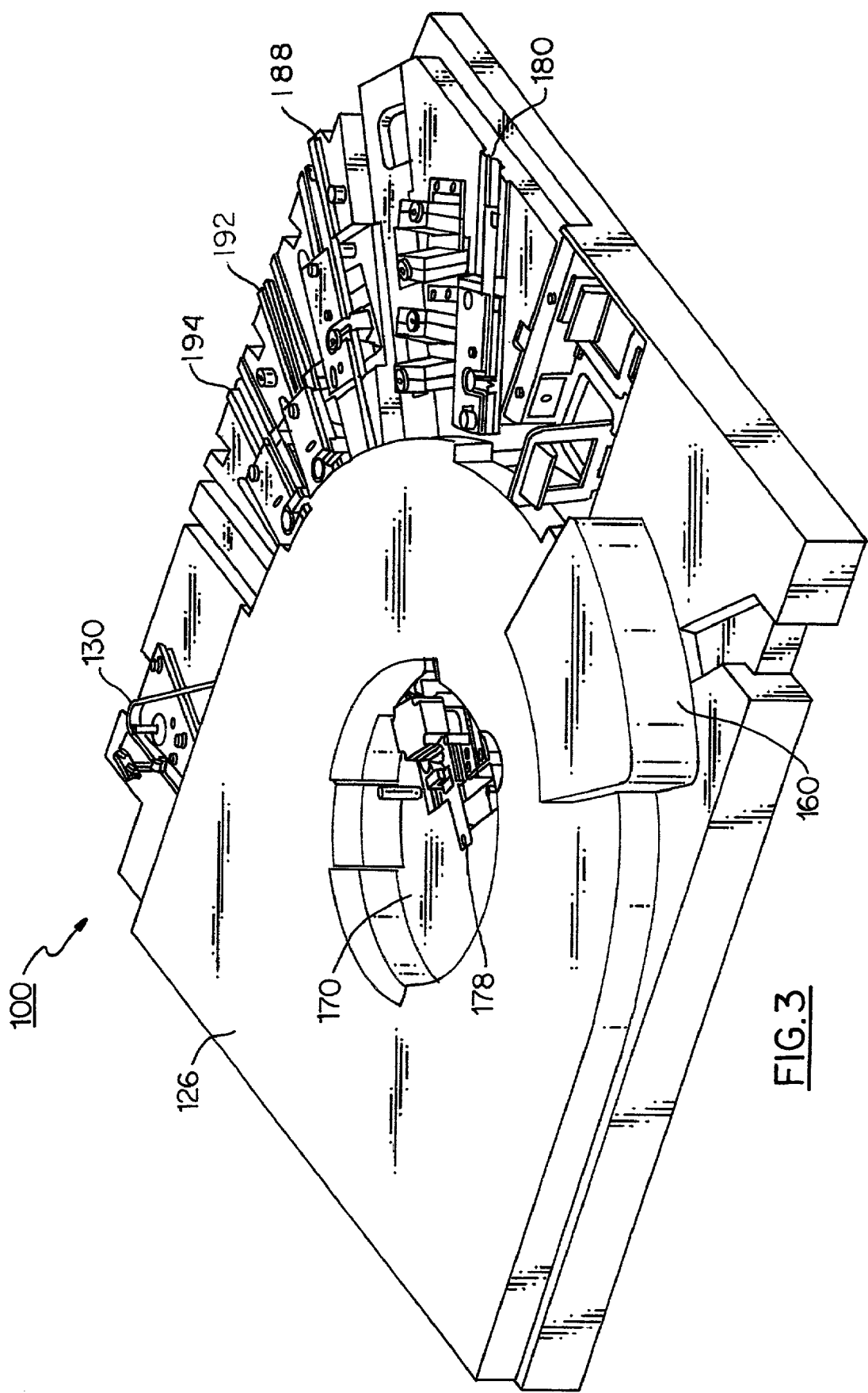
FIG. 3 is a partial top perspective view of an incubator assembly made in accordance with a second embodiment of the invention.

A cover 126 is provided for the ring assembly 104 as partially shown in FIG. 3. The cover 126 provides thermal insulation to aid in temperature control of the interior of the incubator 100.

According to the present embodiment, the inner ring 108 and the outer ring 112 are each independently driven about a common center axis of rotation. As noted previously, the inner ring 108 is a single circular plate-like member which is driven by a belt drive 130, while the outer ring 112 is rotated onto a circular track 138, FIG. 9, using a gear drive. Each of the rings 108,112 are peripherally supported by a set of V-bearings 134, as partially shown in FIGS. 7 and 9, the incubator further including a hot plate 105 onto which each ring 108, 112 is mounted. The hot plate includes, for example, circular track 138, FIG. 9. It should be pointed out that the specific driving mechanisms for each of the rings 108, 112 of the herein described ring assembly 104 do not in and of themselves form an essential part of the present invention. That is to say, a number of different drive mechanisms could be substituted. Providing independent driving capability of each of the inner and outer rings 108, 112, however, is an important aspect of the invention, in that greater flexibility in the loading and shuttling transfer of slide elements 140, 144 into and between each of the slide element positions 116, 118, 122 is provided. This loading and shuttling of slide elements into and within the incubator 100 will be described in greater detail below.

Figure 4:
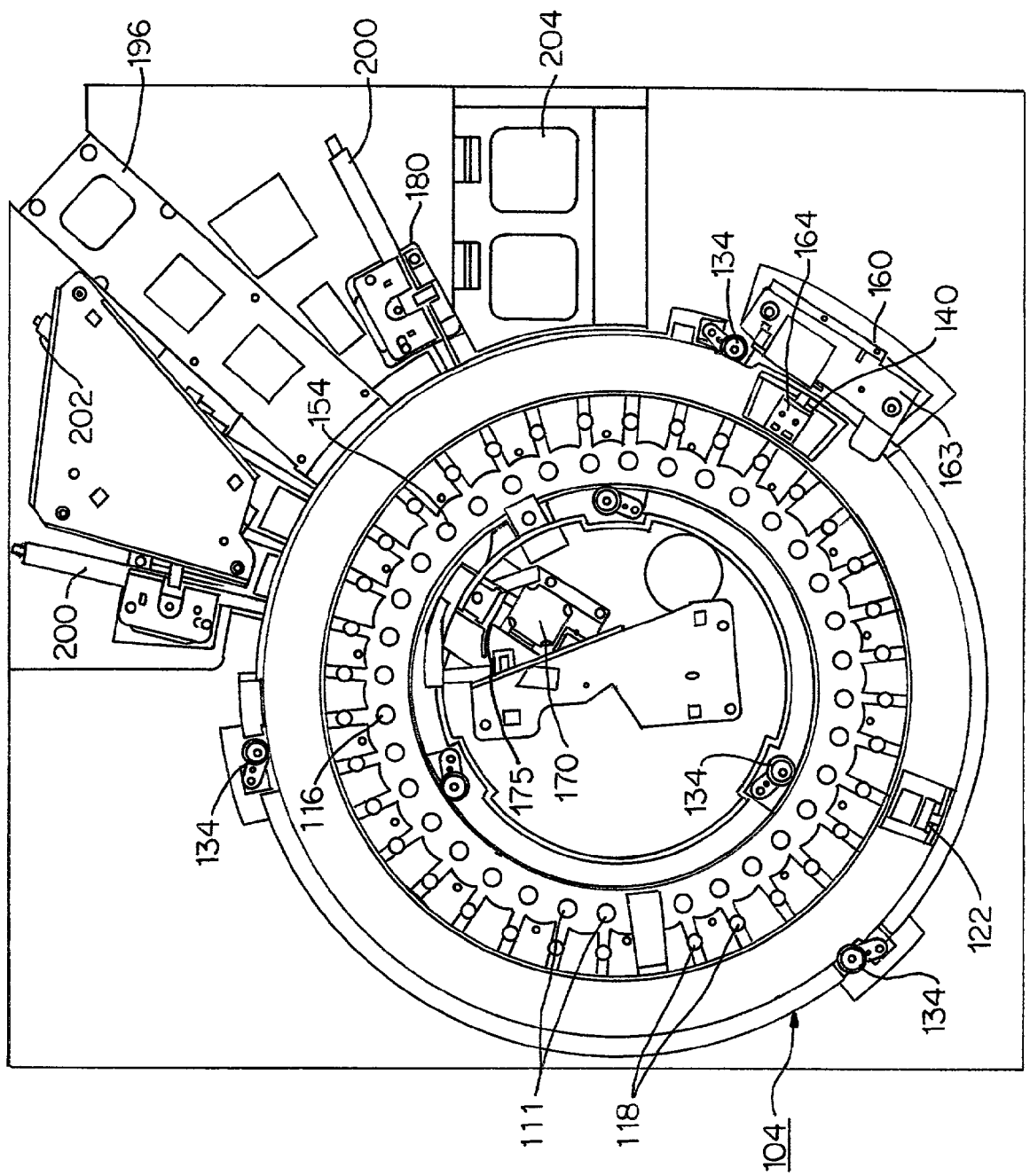
FIG. 4 is a partial top plan view of the incubator of FIG. 3.
Figure 5:
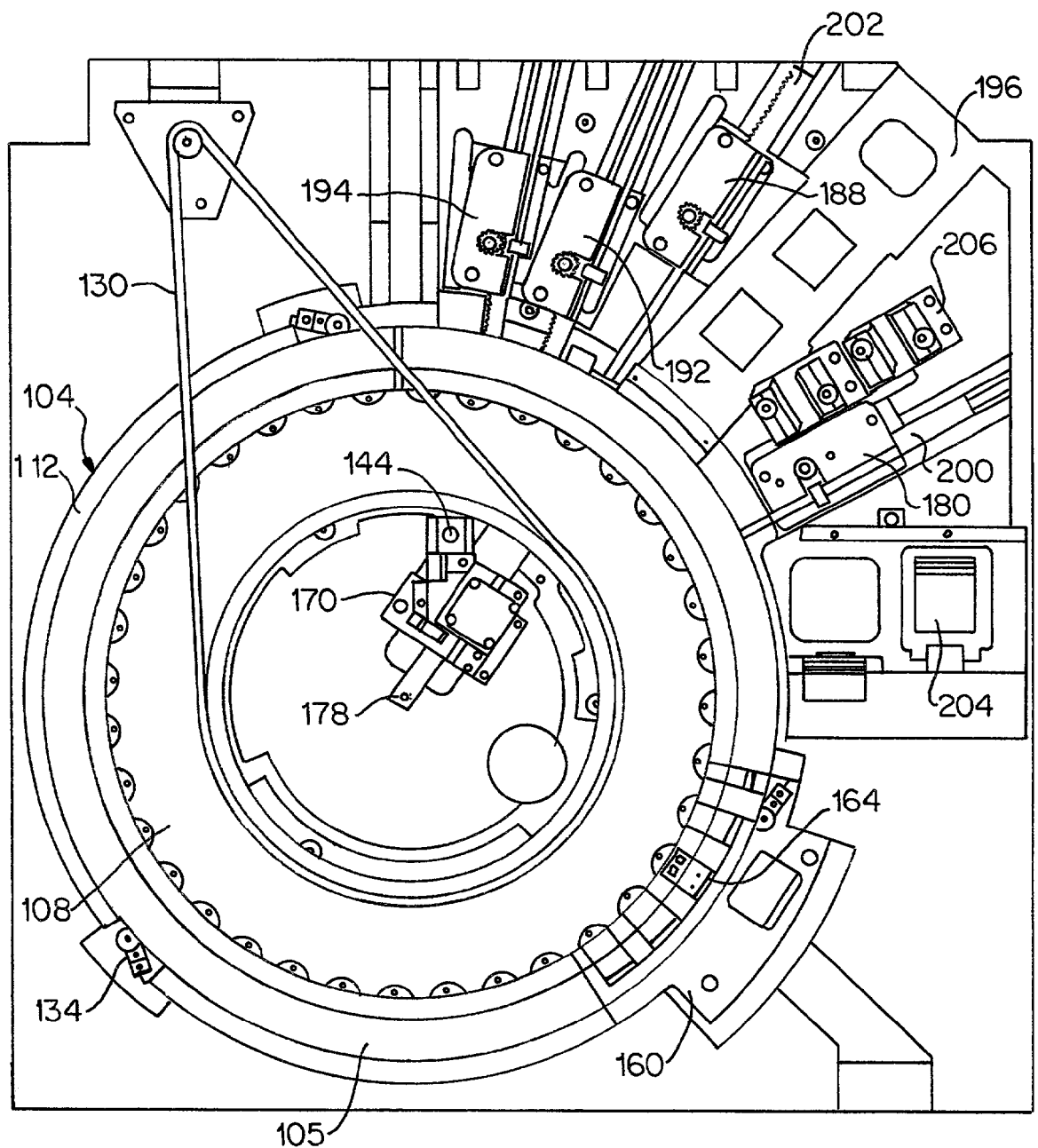
FIG. 5 is the top plan view of the incubator of FIG. 4 with the inner ring of the ring assembly shown.

A single pair of read stations 150, 160, FIGS. 4, 7, are provided for the incubator 100. An inner read station 150, includes a reflectometer 153, partially shown in FIG. 7, which is stationarily located beneath a predetermined circumferential position 154 relative to the inner ring 108 so as to be aligned with the array of rotatably movable inner slide element positions 116. The inner read station 150 therefore permits the reading of either rate chemistry or endpoint colorimetric slide elements 144 at the read location 154 through the opening 111 of an aligned inner slide element position 116. Details relating to the specific operation of the reflectometer 153 and the reading of test elements in general are commonly known in the field, such as described in U.S. Pat. No. 5,034,091, the entire contents of which are herein incorporated by reference.

An outer read station 160 is also provided which is radially adjacent to the outer ring 112. More specifically, the read station 160 is immediately adjacent to each of the outer slide element positions 122, the read station also being positioned at a predetermined circumferential position 164. As detailed below, an electrometer 163 (partially shown in FIG. 4) is provided at the outer read station 160 which allows selective access to a potentiometric slide element 140 after a predetermined incubation time when an element reaches the outer read station 160.

Figure 6:
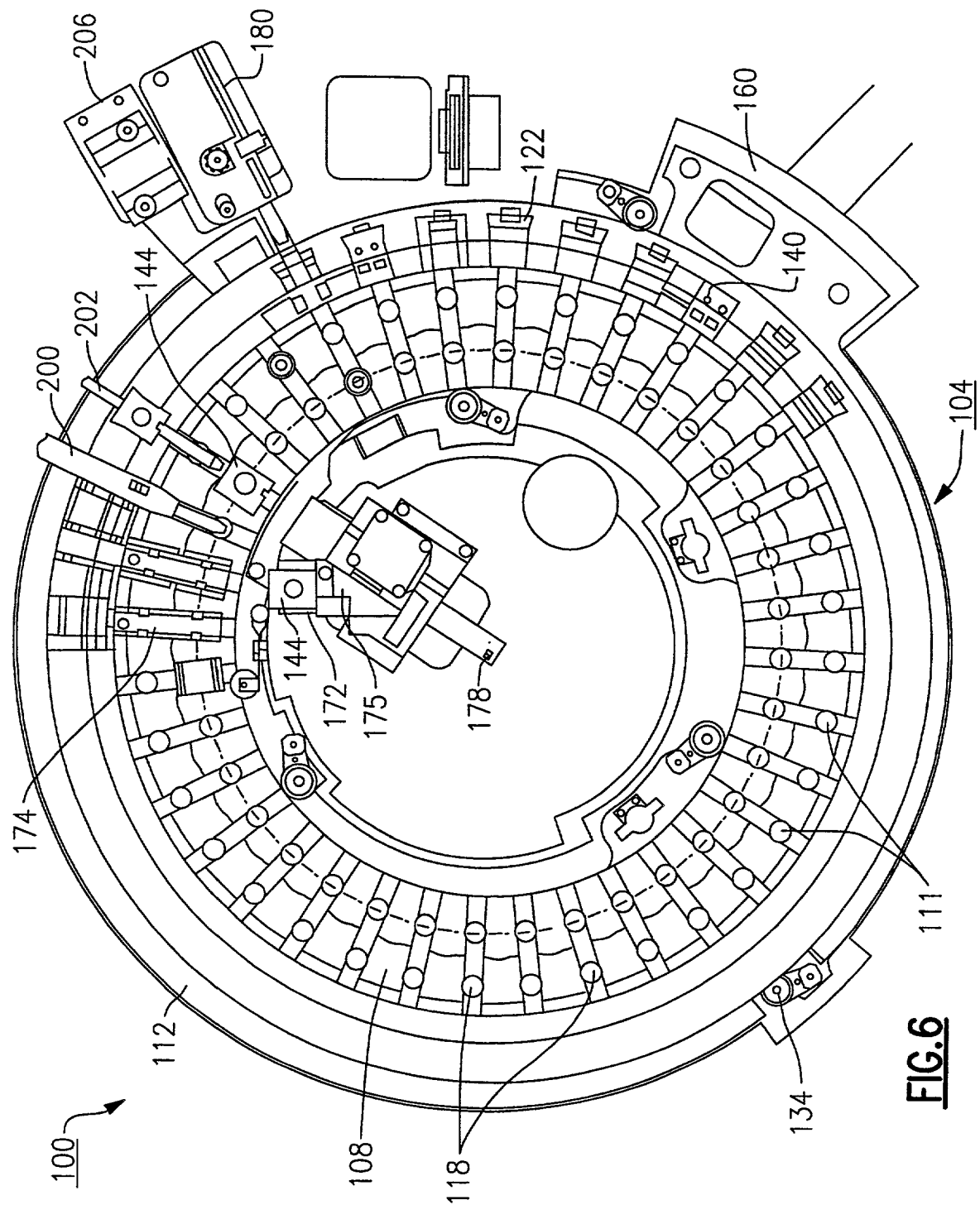
FIG. 6 is an enlarged view of the incubator of FIG. 4.

In addition to the inner and outer read stations 150, 160 and as shown in FIGS. 3-6, 8 and 9, the herein described incubator 100 also includes a wash module 170 located within the inner periphery of the inner ring 108 to permit immuno-rate test capability. The wash module 170 includes an entrance slot 176 that is aligned with a slide pusher blade assembly 188, thereby permitting a slide element 144 to be loaded into the wash station 170 directly from the rotor assembly 104. The wash station 174 further includes a pivoting shuttle assembly 175 which permits a loaded slide element 144 to be shuttled to a wash position 172, as shown in FIG. 6, relative to a wash metering system (not shown) which performs washing thereof. The washed slide element 144 can then be shuttled back to its input position such that the slide element can be transferred back into the inner ring 108 by means of an internal pusher blade assembly 178.

Figure 8:
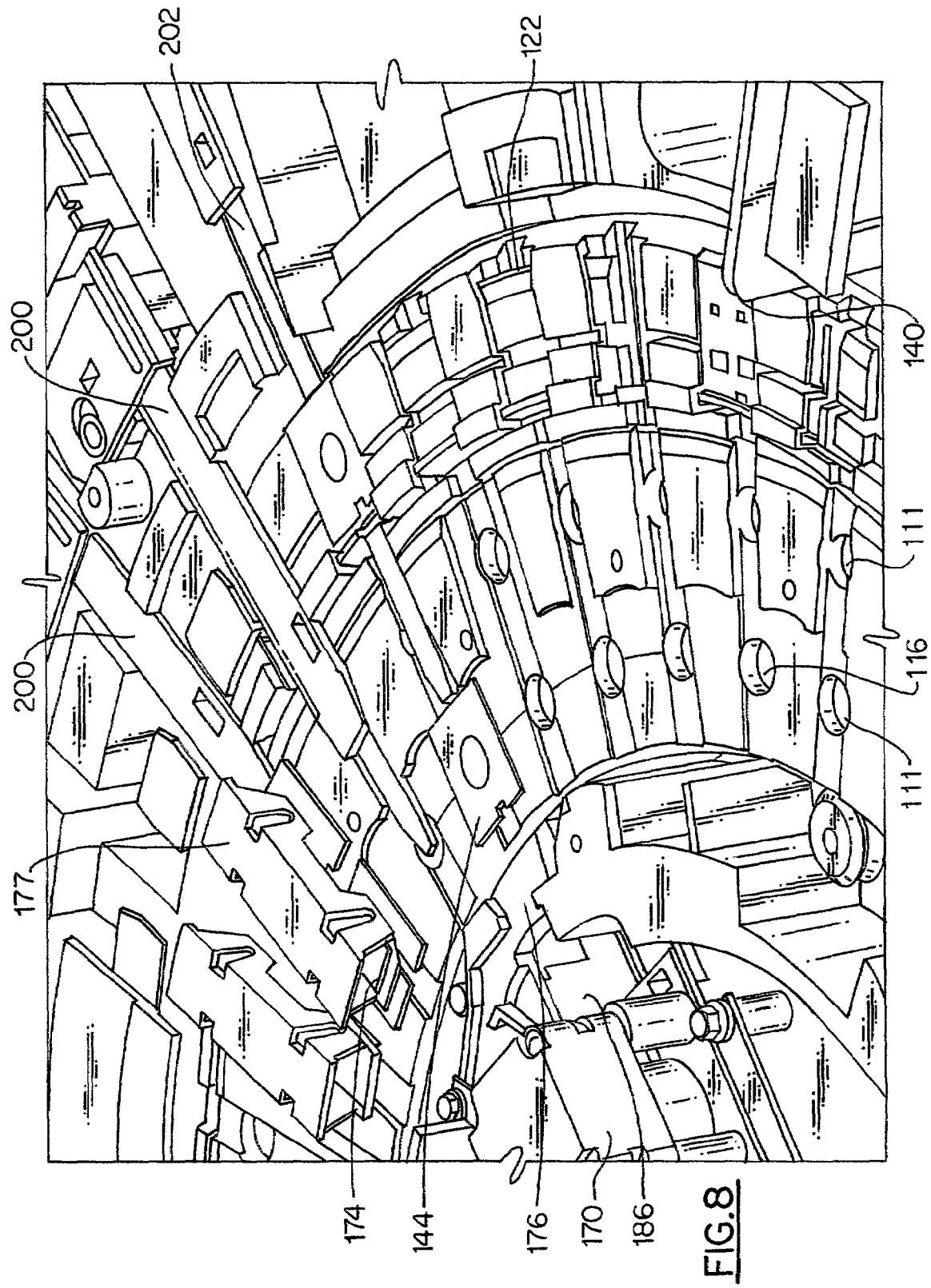
FIG. 8 is an enlarged partial top perspective view of the interior of the incubator of FIGS. 3-7.
Figure 9:
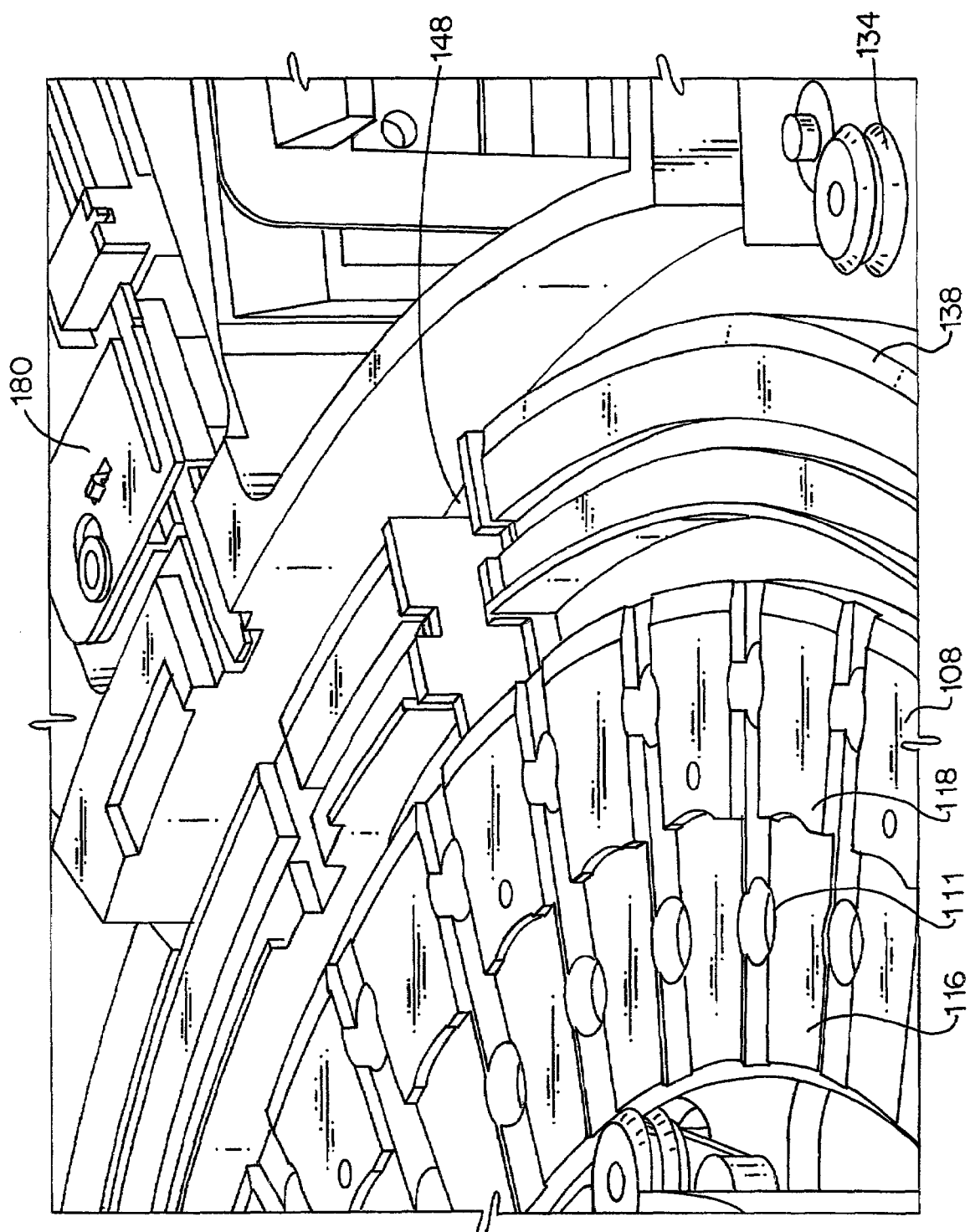
FIG. 9 is an enlarged top perspective view of the outer portion (ring removed) of the incubator of FIGS. 3-8.

Slide or evaporator caps 174, 179 some of which are partially depicted in FIGS. 7 and 8, are provided for all slide positions 116, 118, 122, within the incubator 100, thereby providing evaporation and thermal control for each slide element 140, 144. Details relating to the general operation and function of evaporator caps in a clinical analyzer incubator, including the raising of same to load and unload same into and out of the housing through a cap holder 177, are generally known in the field, as described for example in U.S. Pat. No. 5,034,191, to Porte, and U.S. Pat. No. 4,963,333 to Shaw, et al., incorporated herein in their entirety by reference and therefore do not form an essential part of the claimed invention. For reasons described below, evaporator caps 179 used for potentiometric slide elements 140 are provided for each of the outer slide element positions 122 while evaporator caps 174 used for colorimetric slide elements 144 are provided for each of the slide element positions 116, 118 of the inner ring 108.

In order to effectively shuttle any of the slide elements 140, 144 both into and within the herein described incubator 100, a series of slide element transferring devices are provided.

According to this specific embodiment, and as shown in FIGS. 3, 5-7, and 10-12, a total of five slide transferring devices 180, 183, 188, 192, 194 are provided in relation to a metering station 196.

Figure 10:
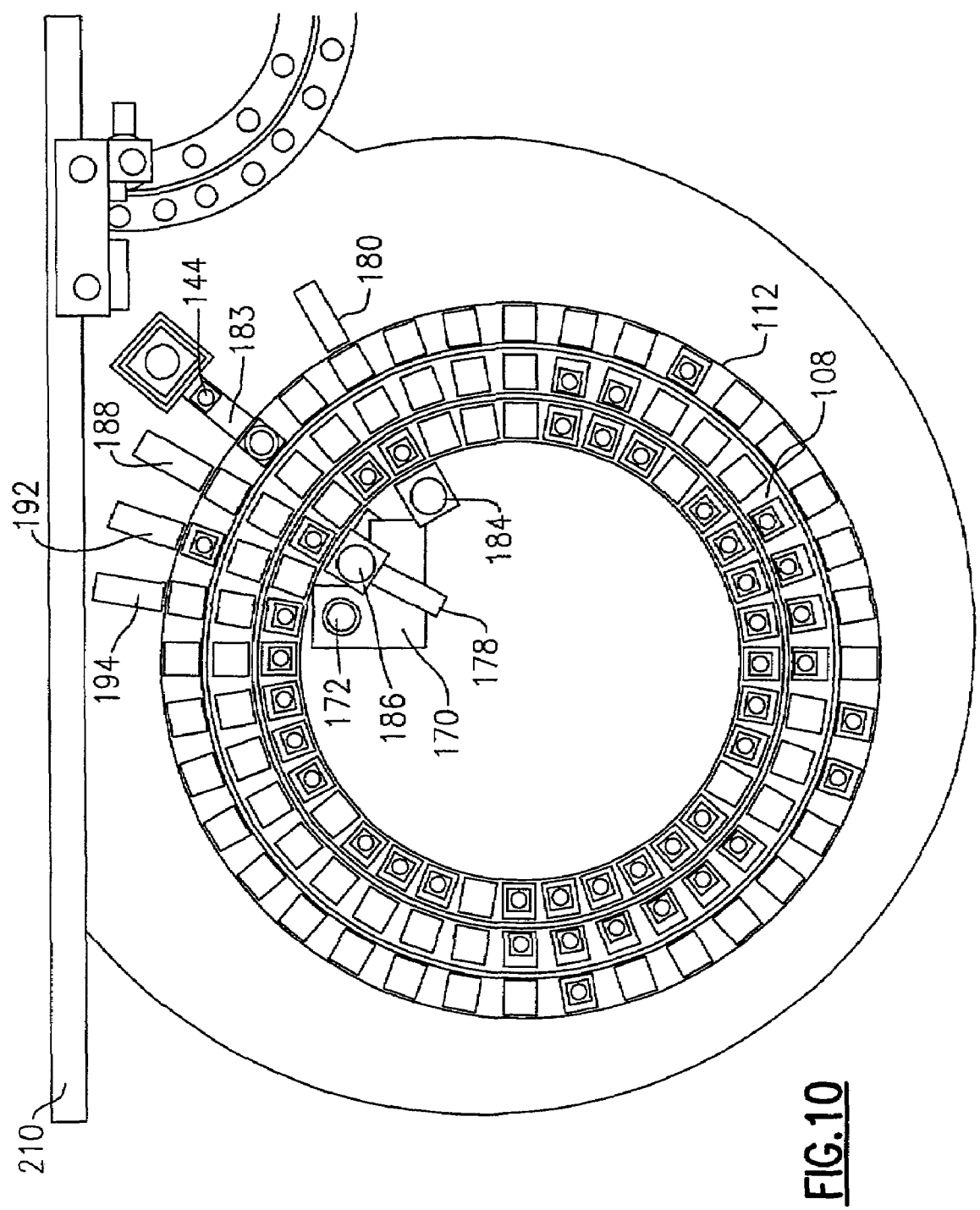
FIGS. 10-12 are pictorial illustrations of the incubator of FIGS. 3-9 illustrating certain interrelationships between test sample loading and positioning of test samples within the incubator.
Figure 11:
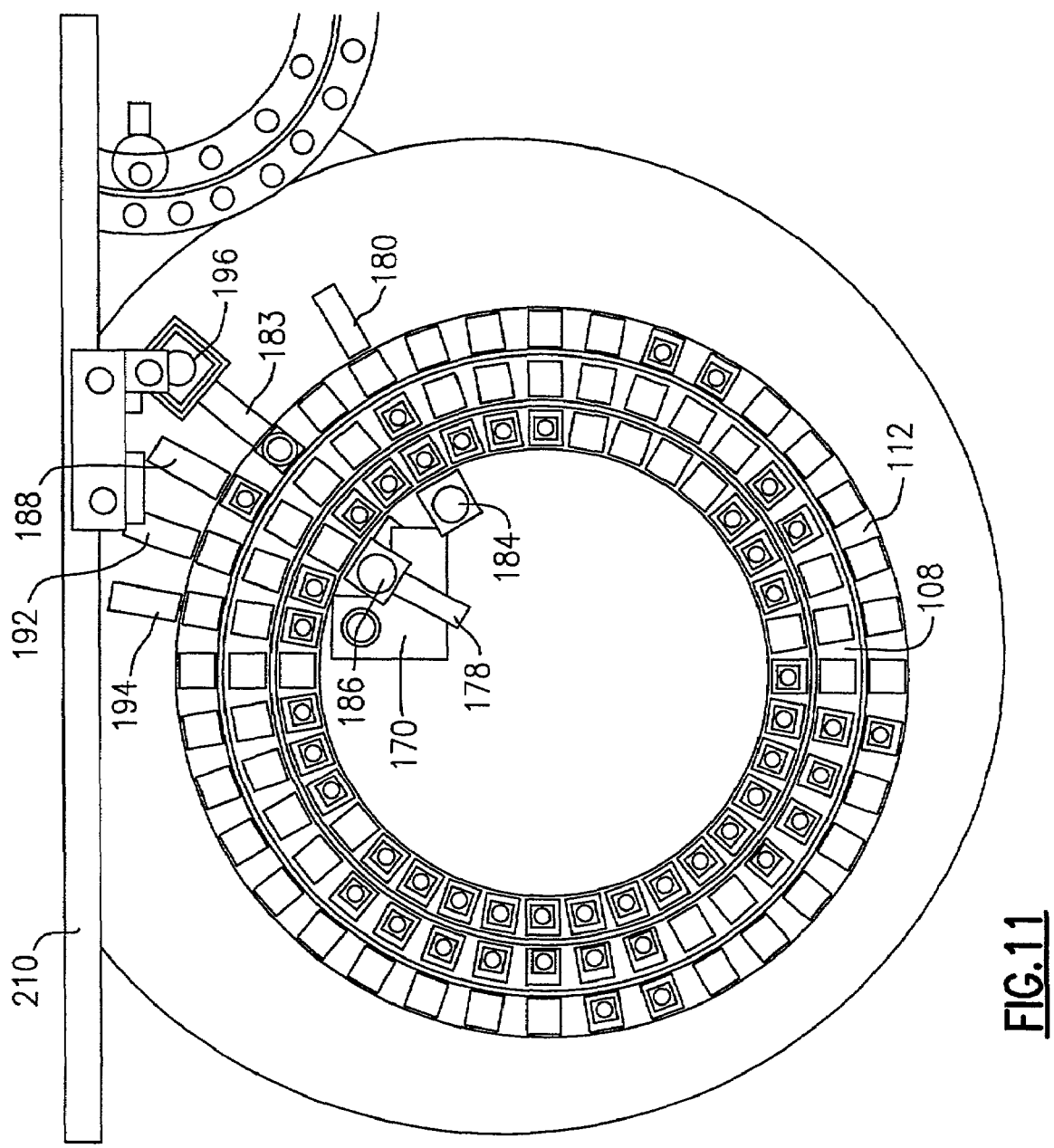
Figure 12:
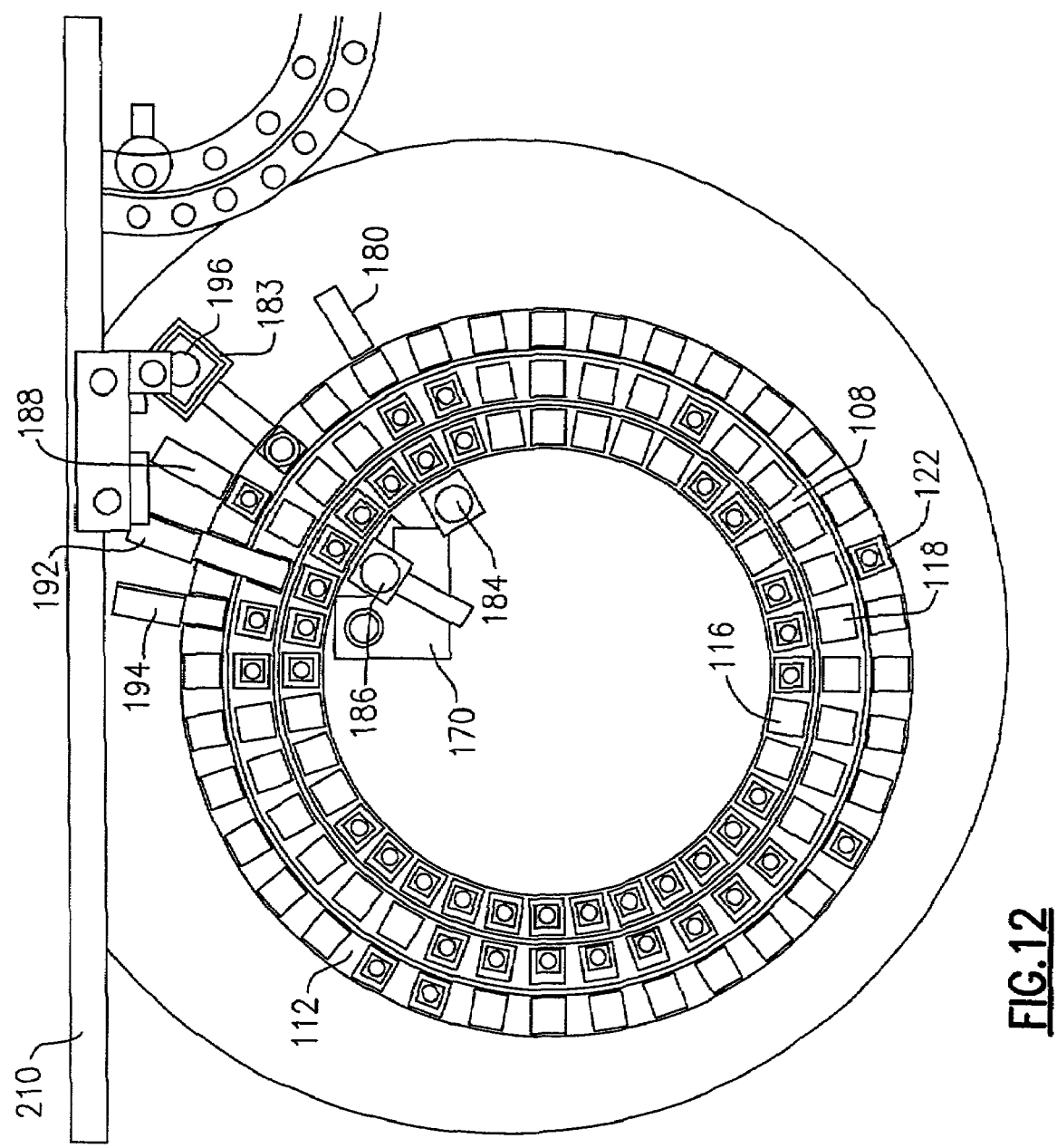

Though shown only pictorially in FIGS. 10-12, one slide transferring device 183 is located directly within the confines of a metering station 196 in order to initially shuttle a metered slide element, either a potentiometric or colorimetric slide element 140,144, into the incubator rotor assembly 104 from a slide cartridge. The slide transferring device 183 operates in a manner which is commonly known, preferably using a reciprocating pusher blade.

The metering station 196 includes a metering head 198 which is disposed along the length of a metering rail 210, FIGS. 10-12. A metering mechanism partially shown pictorially in FIGS. 10-12 permits a patient sample to be delivered along the metering rail 210 from a sample container (not shown) using a proboscis and a disposable metering tip (also not shown) so as to dispense/meter sample onto a slide element 140, 144 provided from a slide supply 204. According to this embodiment, the slide supply 204 retains a plurality of vertically disposed sample cartridges (not shown) which are loaded into a carousel beneath the incubator 100. In a manner commonly known, the slide elements are incremented one at a time to the metering head 198 and are then shuttled into the outer ring 112 of the incubator 100. A series of bar code readers 206 are disposed in relation to the slide supply 204 in order to properly identify the slide elements that are loaded into the incubator 100.

Three (3) of the remaining slide transferring devices 180, 192, 194 are disposed adjacently to the metering station 196 to radially transfer slide elements 140, 144 which have been loaded into the outer ring 112. More particularly, the slide transferring devices 180, 192, and 194 are utilized to transfer non-potentiometric slide elements 144 (either rate chemistry or endpoint) to either the intermediate or inner slide element positions of the inner ring 108 or to the wash station 170. The remaining slide transferring device 180 is disposed on the opposite side of the metering station 196 adjacent to the read station 154. This specific transferring device 180 is preferably adjacent to the inner read station 150 and is used to shuttle calorimetric (e.g., rate) slide elements 144 to an inner eject slot 184 following a final read thereof in order to dispose of the slide elements which are no longer needed and further to create an empty slide element position 116 in the inner ring 108.

For purposes of this embodiment, three of the slide transferring devices 180, 192, 194 include a reciprocating pusher blade 200 having an independent drive mechanism. The pusher blade 200 has a length dimension which permits the end of the blade to engage an edge of a slide element 140, 144 and transfer the slide element into either one of the designated slide positions of the inner and outer rings 108, 112. The slide transferring device 188 also includes a reciprocating pusher blade 202 which is longer than the other pusher blades 200, this device being radially aligned with the entrance slot 176 of the wash station 174.

All of the sample elements, whether potentiometric 140 or calorimetric 144 in type, are initially loaded into the outer ring 112 using the slide transferring device 183, FIGS. 10-12, located in the metering station 196. As intended herein by the present embodiment, the outer slide positions 122 provide an incubation area for potentiometric slide elements 140, as well as certain calorimetric slide elements 144, such as those requiring endpoint testing which requires only a single read be performed at the inner read station 150 following a predetermined incubation interval (e.g., approximately 5 minutes). Other calorimetric slide elements 144, such as those requiring rate chemistries, require a number of reads to be taken by the reflectometer and are preferably shuttled to the inner slide element positions by one of the pusher blade devices 192, 194 after the slide elements 144 have been loaded into the outer ring 112.

In a preferred method of operation and referring to FIGS. 4-12, the incubator 100 of the present embodiment operates in the following manner.

According to this particular embodiment, all spotted (metered) slide elements 140, 144 are initially loaded into the outer ring 112 of the rotor assembly 104 using the slide transferring device 183. Because the outer read station 160 is disposed in relation to the outer ring 112, potentiometric slide elements 140 are not transferred out of the outer ring 112 at any time. These slide elements 140 are therefore maintained in the outer ring 112 during the entire incubation process and are not shuttled to either of the interior slide positions 116, 118.

The gear drive mechanism drives the outer ring 112 incrementally, meaning that the outer ring is advanced one slide position per increment. The inner ring 108, on the other hand, is driven by drive belt 130 at an N+1 increment in which N=one revolution of the ring, thereby incrementing the inner ring with respect to the outer ring 112 per predetermined movement thereof.

This provides a unique and highly efficient means for loading and advancing slides into and within the incubator. That is, the outer ring 112 can be incremented or indexed by one position at a predetermined interval (e.g. approximately 4.5 seconds). The independently driven inner ring 108 can be driven one full revolution plus one position (N+1) over twice the predetermined time interval (approximately 9 seconds) of the outer ring 112. Each of the outer and inner rings 112, 108 can be synchronized at the stopping position. Therefore, the outer ring 112 will have advanced two positions while the inner ring will have advanced one position. For example, the above synchronization When the inner ring 108 stops, up to two slide elements can then be loaded from the outer ring 112 into the inner ring 108 using blades 192, 194. According to a specific protocol, blade 194 will move a slide element from the outer slide element position 122 to a middle slide position 118 while blade 192 will move a slide element from the outer slide element position 122 to the innermost slide position 116. This using of tandem loading technique thereby maximizes the number of slides which can be processed by the incubator. It should be further apparent that the duration of the time intervals can be suitably varied.

In use and following a predetermined incubation interval, the potentiometric slide element 140 is tested at the outer read station 160 by the electrometer 163 in a conventionally known manner as the potentiometric slide element passes the outer read position 164. Following the read, the potentiometric slide element 140 is no longer required according to this embodiment. Therefore, the slide element 140 subsequently passes above an outer dump station 148, shown in FIG. 9, which is provided as a slotted portion of the circular track 138 adjacent the read station 160. As the outer ring 112 rotates in a counterclockwise direction according to the drawings, the slotted portion is exposed allowing the read slide element 140 to drop into the dump station 148.

On the other hand, all reflectometer reads are taken at the read station 150 which is located in alignment with the inner slide element positions 116 as they rotate over the reflectometer 153, FIG. 7. It is desired to get rate chemistry slide elements to the inner ring 108 as soon as possible using one of the slide element transferring devices 192, 194. The endpoint slide elements are shuttled using either of the slide element transferring devices 192, 194 to an intermediate slide element position 118 and subsequently to an inner slide element position 116 for reading and subsequent disposal through either eject slot 184 using the pusher blade 200 of the slide transferring device 180 or an adjacent eject slot 186, FIG. 8, disposed adjacently to the entrance slot 176 of wash station 170 using pusher blade 202 of slide transferring device 188 following a reflectometer read at station 150, FIG. 4.

In the case of an immuno-wash requirement, a spotted calorimetric slide element 144 is initially loaded into the outer ring 112 at the metering station 196. As the outer ring 112 advances incrementally by means of the gear drive mechanism, the slide element 144 is engaged by the pusher blade 202 of slide element transferring device 188 which pushes a slide element which is located in an inner slide element position 116 directly into the wash station 172 through the entrance slot 176 for immuno-rate wash. Preferably, the outer ring load stations 122 are raised in relation to those of the inner ring 108 permitting the pusher blade 202 to pass beneath a potentiometric element 140, as shown more closely in FIG. 8, without engaging therewith.

As previously noted and during wash, the slide element 144 is transferred to the wash station 170 through the entrance slot 176 by means of the pusher blade 202 top an input position. The slide element 144 is then transferred by means of the pivotal shuttle 175 to a wash station and washed before the slide element is pivoted back to the input position and is reinserted back into the inner ring 108 through the slot 176 using the pusher blade 178. It should be noted that in order to perform this particular step, an empty inner slide element position 116 would have to be reserved in the inner ring 108 prior to reinsertion of the washed slide element 144.

| PARTS LIST FOR FIGS. 1-12 | |
|---|---|
| 10 | incubator |
| 12 | linear array |
| 13 | row |
| 14 | load stations |
| 15 | slot or receiving area |
| 16 | row |
| 17 | slot or receiving area |
| 18 | slide element |
| 18A | slide element |
| 18B | slide element |
| 19 | openings |
| 20 | first direction |
| 23 | slide element transferring device |
| 25 | slide element transferring device |
| 30 | read station |
| 31 | slide supply |
| 32 | metering station |
| 33 | staging position |
| 34 | second direction |
| 38 | dump station |
| 50 | incubator assembly |
| 54 | rotor assembly |
| 58 | rotor assembly |
| 100 | incubator |
| 104 | rotor assembly |
| 105 | hot plate |
| 108 | inner ring |
| 112 | outer ring |
| 116 | inner slide element position |
| 118 | intermediate slide element position |
| 122 | outer slide element position |
| 126 | cover |
| 130 | drive belt |
| 134 | V-bearings |
| 138 | track |
| 140 | potentiometric slide element |
| 142 | dump station |
| 144 | colorimetric slide element |
| 148 | slotted portion |
| 150 | inner read station |
| 153 | reflectometer |
| 154 | read location |
| 160 | outer read station |
| 163 | electrometer |
| 164 | read position |
| 170 | wash station |
| 172 | wash position |
| 174 | evaporator caps |
| 175 | shuttle assembly |
| 176 | entrance slot |
| 177 | holder for evaporator caps |
| 178 | pusher blade |

| -continued | |
|---|---|
| PARTS LIST FOR FIGS. 1-12 | |
| 179 | evaporator caps |
| 180 | slide transferring device |
| 183 | slide transferring device |
| 184 | eject slot |
| 186 | eject slot |
| 188 | slide transferring device |
| 192 | slide transferring device |
| 194 | slide transferring device |
| 196 | metering station |
| 198 | metering head |
| 200 | reciprocating pusher blade |
| 202 | reciprocating pusher blade |
| 204 | slide element supply |
| 206 | bar code readers |
| 210 | metering rail |

Though the preceding has been described in terms of certain specific embodiments, it will be apparent that certain variations and modifications are possible which still embody the inventive concepts of the present invention. For example, any of the read stations can be otherwise disposed. For example, the reflectometer can be located in a read position which is fixedly held relative to the outer incubator ring. In this version, the electrometer can be located within the incubator; that is, radially inward of the inner ring. The potentiometric slide element 140 can be selectively picked from an outer slide element position 122 by means of a conventionally known picker assembly (not shown) and transferred to a read station (not shown) to then be read by the electrometer. The potentiometric slide element 140 following the read operation can then be shuttled by known means to an external dump station (not shown) for disposal thereof.

The invention claimed is:

1. A sequential tandem incubator for use in a clinical analyzer, said incubator comprising:
    an inner ring and an outer ring, said outer ring including a first plurality of circumferentially disposed slide element receiving areas and said inner ring including a second plurality of circumferentially disposed slide element receiving areas, each of said first and second pluralities of slide element receiving areas being radially adjacent to one another on a common horizontal plane;
    at least one first drive mechanism for driving at least one of said inner and outer rings rotationally about at least one axis and within said common horizontal plane; and
    at least two second drive mechanisms for selectively moving slide elements in a radial direction exclusively within said common horizontal plane into and out of said incubator and between said first and second plurality of said circumferentially disposed slide element receiving areas in order to increase throughput of said incubator, each of said at least two second drive mechanisms including at least one reciprocating pusher blade assembly for loading slide elements into one of said inner ring and said outer ring and for moving slide elements between said inner ring and said outer ring.

2. An incubator as recited in claim 1, wherein said at least one reciprocating pusher blade assembly of said at least two second drive mechanisms can selectively and radially remove at least one slide element from said incubator for later reinsertion therein.

3. An incubator as recited in claim 1, including a plurality of dry slide elements, each of said dry slide elements having a volume of a patient sample fluid metered thereupon prior to entry into said incubator.

4. An incubator as recited in claim 1, wherein said at least one first drive mechanism includes a drive belt wrapped about the periphery of at least one of said inner and outer rings.

5. An incubator as recited in claim 1, wherein said inner and outer rings are independently driven relative to one another by said at least one first drive mechanism.

6. An incubator as recited in claim 1, wherein at least two load positions of a slide element receiving area differ in height relative to one another.

7. An incubator as recited in claim 1, wherein at least one reciprocating pusher blade assembly is radially disposed on the interior of said inner ring.

8. An incubator as recited in claim 1, wherein a plurality of second drive mechanisms are disposed at predetermined circumferential locations adjacent to said inner and outer rings, each of said second drive mechanisms including a reciprocating pusher blade assembly.

9. An incubator as recited in claim 8, wherein each of said plurality of second drive mechanisms are circumferentially disposed at predetermined locations about said outer ring, wherein the reciprocating pusher blade assemblies of at least two of said plurality of second drive mechanisms can load and unload at least one slide element in relation to said incubator and can further radially move at least one slide element between slide element receiving areas as the inner ring and outer ring are rotated by the first drive mechanism in order to move each of said first and second pluralities of slide elements receiving areas being movable into registration with said second drive mechanism.

10. An incubator as recited in claim 1, wherein each of said inner and outer rings are supported for rotation by said at least one first drive mechanism about a central axis of an incubator housing.

11. An incubator as recited in claim 10, wherein at least one of said first and second pluralities of circumferentially disposed slide element receiving areas includes at least two radially adjacent slide element receiving stations wherein said at least one reciprocating pusher blade assembly of one of said second drive mechanisms can selectively radially move said at least one slide element between at least said at least two adjacent slide element receiving areas.

12. An incubator as recited in claim 11, wherein at least one reciprocating pusher blade assembly of said at least two second drive mechanisms radially shuttles slide elements into and out of said incubator.

13. An incubator as recited in claim 12, wherein at least two of said at least two second drive mechanisms are circumferentially disposed in relation to at least one of said inner ring and said outer ring.

14. An incubator as recited in claim 12, wherein said at least one reciprocating pusher blade assembly of each of said at least two second drive mechanisms is disposed in relation to said incubator to shuttle at least one slide element into at least one slide element receiving station.

15. An incubator as recited in claim 12, wherein said at least one reciprocating pusher blade assembly of each of said two second drive mechanisms can move at least two radially disposed slide elements into radially adjacent slide element receiving areas or receiving stations simultaneously.

16. An incubator as recited in claim 12, including a supply of stacked slide elements, at least one said second drive mechanism being disposed adjacent to said slide element supply.

17. An incubator as recited in claim 11, including at least one read station disposed in relation to one of said inner and outer rings, such that said at least one first drive mechanism can rotate one slide element receiving area into a read position, said at least one reciprocating pusher blade assembly enabling a slide element to be selectively and radially moved from a radially adjacent slide element receiving area into the read position.

18. An incubator as recited in claim 17, wherein said read station includes a device capable of measuring an electrical property of a slide element.

19. An incubator as recited in claim 18, wherein said device is an electrometer.

20. An incubator as recited in claim 17, including a dump station radially adjacent said read station.

21. An incubator as recited in claim 17, wherein said read station includes a device capable of detecting an optical property of a test slide element.

22. An incubator as recited in claim 21, wherein said device is a reflectometer.

23. A method of incubating and reading test slide elements using a sequential random incubator in a clinical analyzer, said sequential random incubator comprising an inner ring and an outer ring, said outer ring including a first plurality of circumferentially disposed slide element receiving areas and said inner ring including a second plurality of circumferentially disposed slide element receiving areas, each of said first and second pluralities of slide element receiving areas being radially adjacent to one another within a common horizontal plane, said method comprising the steps of:

radially loading at least one slide element into an empty slide element receiving area;

rotating at least one of said inner and outer rings within the common horizontal plane; and moving said at least one slide element radially between said first and second pluralities of radially adjacent slide element receiving areas of said incubator within said common horizontal plane so as to improve the throughput of said incubator, wherein said radially loading and said radially moving steps are performed using at least two reciprocating pusher blade assemblies disposed in relation to said incubator and within said common horizontal plane.

24. A method as recited in claim 23, including the additional steps of:

reading a first slide element which has been rotated into alignment with a read station;

radially driving an adjacent second slide element into alignment with said read station using at least one of said reciprocating pusher blade assemblies; and reading said second slide element.

25. A method as recited in claim 24, including the step of dumping each of said slide elements from said inner ring after said reading steps.

26. A method as recited in claim 25, including the step of radially loading at least one slide element from the outer ring into said inner ring using at least one reciprocating pusher blade assembly after said dumping step.

27. A method as recited in claim 26, wherein said loading step includes the step of simultaneously radially shuttling at least two adjacent test slide elements into radially adjacent slide element receiving areas.

* * * * *